(12) United States Patent
Dorn et al.

(10) Patent No.: US 8,198,259 B2
(45) Date of Patent: Jun. 12, 2012

(54) TREATMENT OF NEUROLOGICAL DISORDERS BY DSRNA ADMINISTRATION

(75) Inventors: Gabriele Dorn, Rotkreutz (CH);
Pamposh Ganju, London (GB);
Jonathan Hall, Dornach (CH); Maria Wanda Hemmings, Bettingen (CH);
William Leonard Wishart, Allschwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/289,334

(22) Filed: Nov. 4, 2011

(65) Prior Publication Data
US 2012/0053230 A1 Mar. 1, 2012

Related U.S. Application Data

(62) Division of application No. 11/779,098, filed on Jul. 17, 2007, now Pat. No. 8,129,354.

(51) Int. Cl.
*C12N 15/11* (2006.01)
*C07H 21/02* (2006.01)
*C07H 21/04* (2006.01)
(52) U.S. Cl. .................. 514/44; 536/24.1; 536/24.5
(58) Field of Classification Search .............. 514/44; 536/24.1, 24.5
See application file for complete search history.

(56) References Cited

U.S. PATENT DOCUMENTS

| | | | |
|---|---|---|---|
| 6,119,124 A | 9/2000 | Broder et al. | |
| 6,240,409 B1 | 5/2001 | Aiken | |
| 6,658,423 B1 | 12/2003 | Pugh et al. | |
| 7,562,186 B2 | 7/2009 | Li et al. | |
| 2005/0108339 A1 | 5/2005 | Gleeson et al. | |
| 2006/0030534 A1 | 2/2006 | Dorn et al. | |
| 2006/0128644 A1 | 6/2006 | Barclay et al. | |
| 2006/0135453 A1 | 6/2006 | Bologna et al. | |
| 2007/0085716 A1 | 4/2007 | Bar-Yossef et al. | |

FOREIGN PATENT DOCUMENTS

| | | |
|---|---|---|
| EP | 308066 A2 | 3/1989 |
| WO | WO 02/067858 A2 | 9/2002 |
| WO | WO 02/100328 A2 | 12/2002 |
| WO | WO 02/100329 A2 | 12/2002 |
| WO | WO 03/070895 A2 | 8/2003 |

OTHER PUBLICATIONS

Simpson et al.; "Intrathecal Administration of Antisense Oligodeoxynucleotide Inhibits c-fos Protein Expression in the Dorsal Horn of Neuropathic rats When Given Prior to Sciatic Nerve Ligation"; Neurosurgery; 41(3):731 (1997).
Soutschek et al.; "Therapeutic silencing of an endogenous gene by systemic administration of modified siRNAs"; Nature; 432:173-178 (2004).
Standifer et al; "Selective loss of delta opioid analgesia and binding by antisense oligodeoxynucleotides to a delta opioid receptor"; Neuron; 12:805-810 (1994).
Tan et al.; "Gene knockdown with intrathecal siRNA of NMDA receptor NR2B subunit reduces formalin-induced nociception in the rat"; Gene Therapy; 12:59-66 (2005).
Tan et al; "Therapeutic potential of RNA interference in pain medicine"; Open Pain Journal; 2:57-63 (2009).
Tseng et al; "Antisense oligodeoxynucleotide to a delta-opioid receptor selectively blocks the spinal antinociception induced by delta-, but not mu- or kappa-opioid receptor agonists in the mouse"; European Journal of Pharmacology; 258:R1-R3 (1994).
U.S. Appl. No. 10/447,839, filed May 29, 2003; "Decision on Appeal—With Supporting Documents"; (2010).
Vickers et al.; "Efficient Reduction of Target RNAs by Small Interfering RNA and RNase H-dependent Antisense Agents"; The Journal of Biological Chemistry; 278:7108-7118 (2003).
Wahlestedti; "Antisense oligonucleotide strategies in neuropharmacology"; TiPS 15:42-46 (1994).
"Webster's Encyclopedic Unabridged Dictionary of the English Language"; Copyright 1989 by dilithium Press, Ltd. Published by Portland House 1989.; p. 43.
Xia et al.; "SiRNA-Mediated Gene Silencing in Vitro and In Vivo"; Nature Biotech; 20:1006-1010 (2002).
Yu et al.; "RNA interference by expression of short-interfering RNAs and hairpin RNAs in mammalian cells"; PNAS of USA, National Academy of Science, Washington, US; 99(9):30 (2002).
Zhang et al; "DNA-dependent protein kinase (DNA-PK) phosphorylates nuclear DNA helicase II/RNA helicase A and hnRNP proteins in an RNA-dependent manner"; Nucleic Acids Research; 32(1):1-10 (2004).
Accession No. AF084975; "*Rattus norvegicus* P2X3b receptor mRNA, alternatively spliced, complete cds"; ROD: Aug. 9, 1999.
Akopian et al; "Peripheral Nervous System-specific Genes Identified by Subtractive cDNA Cloning"; Journal of Biological Chemistry; 270(36):21264-21270 (1995).
Barclay et al; "Functional Downregulation of P2X3 Receptor Subunit in Rat Sensory Neurons Reveals a Significant Role in Chronic Neuropathic and Inflammatory Pain"; Journal of Neuroscience; 22(18):8139-8147 (2002).
Bertrand et al.; "Comparison of antisense oligonucleotides and siRNAs in cell culture and in vivo"; Biochemical and Biophysical Research Communications; 296:1000-1004 (2002).
Bilsky et al; "Selective blockade of peripheral delta opioid agonist induced antinociception by intrathecal administration of delta receptor antisense oligodeoxynucleotide"; Neuroscience Letters; 220:155-158 (1996).
Bumcrot et al.; "RNAi therapeutics: a potential new class of pharmaceutical drugs"; Nature Chemical Biology—Review; 2(12):711-719 (2006).
Caplen et al.; "Specific Inhibition of Gene Expression by Small Double-Stranded RNAs in Invertebrate and Vertebrate Systems"; PNAS; 98(17):9742-9747 (2001).
Chen et al; "A P2X purinoceptor expressed by a subset of sensory neurons"; Nature; 377:428-431 (1995).

(Continued)

*Primary Examiner* — Terra Cotta Gibbs
(74) *Attorney, Agent, or Firm* — Frank Wu; Novartis AG

(57) ABSTRACT

The present invention relates to methods to treat neurological disorders comprising intrathecal injection of an effective amount of a double-stranded (ds) RNA into a subject in need, wherein the dsRNA inhibits the expression of a target gene and to pharmaceutical compositions useful for such treatment.

22 Claims, No Drawings

OTHER PUBLICATIONS

Chiasson et al; "The Application of Antisense Oligonucleotide Technology to the Brain: Some Pitfalls"; Cellular and Molecular Neurobiology; 14(5): 507-521 (1994).
Chizh et al.; "P2X Receptors and Nociception"; Pharmacological Reviews; 53(4):553-568 (2000).
Christoph et al.; "Silencing of vanilloid receptor TRPV1 by RNAi reduces neuropathic and visceral pain in vivo"; Biochemical and Biophysical Research Communications; 350:238-243 (2006).
Collo et al; "Cloning of P2X5 and P2X6 Receptors and the Distribution and Properties of an Extended Family of ATP-Gated Ion Channels"; Journal of Neuroscience; 16(8):2495-2507 (1996).
Dorn et al; "siRNA relieves chronic neuropathic pain"; Nucleic Acids Research; 32(5):e49 (pp. 1-6) (2004—published online Mar. 16, 2004).
Dorn et al.; "Specific Inhibition of the Rate Ligand-Gated Ion Channel P2X3 Function Via Methoxyethoxy-Modified Phosphorothioated Antisense Oligonucleotides"; Antisense and Nuclid Acid Drug Develop.; 11:165-174 (2001).
Elbashir et al.; "Functional anatomy of siRNAs for mediating efficient RNAi in *Drosophila melanogaster* embryo lysate"; The EMBO Journal; 20(23):6877-6888 (2001).
Elbashir et al.; "RNA interference is mediated by 21- and 22-nucleotide RNAs"; Genes & Development; 15:188-200 (2001).
Esau; "Inhibition of microRNA with antisense oligonucleotides"; Methods; 44:55-60 (2008).
Far et al.; "The activity of siRNA in mammalian cells is related to structural target accessibility: a comparison with antisense oligonucleotides"; Nucleic Acids Research; 31(15):4417-4424 (2003).
Farah; "RNAi Silencing in Mouse Models of Neurodegenerative Diseases"; Current Drug Delivery; 4:161-167 (2007).
Gan et al.; "Specific interference of gene function by double-stranded RNA in neuronal cell lines"; Abstracts of the Society for Neuroscience, Society for Neuroscience, Washington, DC, US; 27(2):2051 (2001).
Ganju et al.; "Potenial applications of siRNA for pain therapy"; Expert Opinion Biol. Ther.—Review; 4(4):531-542 (2004).
Gever et al; "AF-353, a novel, potent and orally bioavailable P2X3/P2X2/3 receptor antagonist"; British Journal of Pharmacology; 160:1387-1398 (2010).
Hall; "Application of RNAi in Biomedical Research"; Chimia; 59(11):803-807 (2005).
Hammond et al; "Argonaute2, a Link Between Genetic and Biochemical Analyses of RNAi"; Science; 293:1146-1150 (2001).
Hammond et al.; "Post-Transcriptional Gene Silencing by Double-Stranded RNA"; Nature—Reviews; 2:110-119 (2001).
Hemmings-Mieszczak et al; "Independent combinatorial effect of antisense oligonucleotides and RNAi-mediated specific inhibition of the recombinant Rat P2X3 receptor"; Nucleic Acids Research; 31(8):2117-2126 (2003).
Honore et al.; "Analgesic profile of intrathecal P2X3 antisense oligonucleotide treatment in chronic inflammatory and neuropathic pain states in rats"; Pain; 99:11-19 (2002).
Huang et al; "Antisense of c-fos gene attenuates Fos expression in the spinal cord induced by unilateral constriction of the sciatic nerve in the rat"; Neuroscience Letters; 263:61-64 (1999).
Huang et al; "Intrathecal treatment with MK-801 suppresses thermal nociceptive responses and prevents c-fos immunoreactivity induced in rat lumbar spinal cord neurons"; Neurological Research; 21:593-598 (1999).

Hunter et al; "C-fos antisense oligodeoxynucleotide increases formalin-induced nociception and regulates preprodynorphin expression"; Neuroscience; 65(2):485-492 (1995).
Jain; "Gene Therapy for Pain"; Expert Opinion Biol Ther; 8(12):1855-1866 (2008).
Khasar et al; "Selective attenuation of mu-opioid receptor-mediated effects in rat sensory neurons by intrathecal administration of antisense oligodeoxynucleotides"; Neuroscience Letters; 218:17-20 (1996).
Krishtal et al; "Receptors for ATP in rat sensory neurones: the structure-function relationship for ligands"; British Journal of Pharmacology; 95:1057-1062 (1988).
Kurreck; "Antisense and RNA interference approaches to target validation in pain research"; Current Opinion in Drug Discovery & Development; 7(2):179-187 (2004).
Lewis et al; "Coexpression of P2X2 and P2X3 receptor subunits can account for ATP-gated currents in sensory neurons"; Nature; 377:432-435 (1995).
Li et al; "Zn2+ potentiates excitatory action of ATP on mammalian neurons"; Proc Natl Acad Sci USA; 90:8264-8267 (1993).
Liang et al.; "P2X receptors and modulation of pain transmission: Focus on effects of drugs and compounds used in traditional Chinese medicine"; Neurochemistry International; 57:705-712 (2010).
Liu et al; "Suppression of Ischemia-induced Fos Expression and AP-1 Activity by an Antisense Oligodeoxynucleotide to c-fos mRNA"; Annals of Neurology; 36(4):566-576 (1994).
Luo et al.; "An efficient intrathecal delivery of small interfering RNA to the spinal cord and peripheral neurons"; Molecular Pain; 1:29 (1-8) (2005).
Miyagishi et al.; "U6 Promoter-Driven siRNAs with Four Uridine 3' Overhangs Efficiently Suppress Targeted Gene Expression in Mammalian Cells"; Nature Biotech; 20:497-500 (2002).
Narita et al; "Stimulation of spinal delta-opioid receptors in mice selectively enhances the attenuation of delta-opioid receptor-mediated antinociception by antisense oligodeoxynucleotide"; European Journal of Pharmacology; 284:185-189 (1995).
Natt; "siRNAs in drug discovery: Target validation and beyond"; Current Opinion in Molecular Therapeutics; 9 (3):242-247 (2007).
Pilowsky et al; "Antisense oligonucleotides: a new tool in neuroscience"; Clinical and Experimental Pharmacology and Physiology; 21:935-944 (1994).
Porreca et al.; "A comparison of the potential role of the tetrodotoxin-insensitive sodium channels, PN3/SNS and NaN/SNS2, in rat models of chronic pain"; Proc. Natl. Acad. Sci. USA; 96:7640-7644 (1999).
Ralevic et al; "Receptors for Purines and Pyrimidines"; Pharmacological Reviews; 50(3):413-492 (1998).
Robertson et al; "Characterization of a P2X-purinoceptor in cultured neurones of the rat dorsal root ganglia"; British Journal of Pharmacology; 118:951-956 (1996).
Rohl et al.; "RNA interference in pain research"; Journal of Neurochemistry; 99:371-380 (2006).
Saetrom; "Predicting the efficacy of short oligonucleotides in antisense and RNAi experiments with boosted genetic programming"; Bioinformatics; pp. 1-11 (2004).
Sah et al; "Therapeutic potential of RNA interference for neurological disorders"; Life Sciences; 79:1773-1780 (2006).
Scherer et al.; "Approaches for the sequence-specific knockdown of mRNA"; Nature Biotechnology; 21 (12):1457-1465 (2003).

SEQUENCE LISTING

```
<160> NUMBER OF SEQ ID NOS: 31

<210> SEQ ID NO 1
<211> LENGTH: 18
<212> TYPE: DNA
<213> ORGANISM: homo sapiens

<400> SEQUENCE: 1
ctccatccag ccgagtga                                                 18

<210> SEQ ID NO 2
<211> LENGTH: 18
<212> TYPE: DNA
<213> ORGANISM: homo sapiens

<400> SEQUENCE: 2
ctacagccat ccgcgtga                                                 18

<210> SEQ ID NO 3
<211> LENGTH: 18
<212> TYPE: DNA
<213> ORGANISM: homo sapiens

<400> SEQUENCE: 3
ggccatccac agtcttct                                                 18

<210> SEQ ID NO 4
<211> LENGTH: 18
<212> TYPE: DNA
<213> ORGANISM: homo sapiens

<400> SEQUENCE: 4
ccttacctgc tagctggc                                                 18

<210> SEQ ID NO 5
<211> LENGTH: 18
<212> TYPE: DNA
<213> ORGANISM: homo sapiens

<400> SEQUENCE: 5
ctccatccag ccgagtga                                                 18

<210> SEQ ID NO 6
<211> LENGTH: 18
<212> TYPE: DNA
<213> ORGANISM: homo sapiens

<400> SEQUENCE: 6
ctacagccat ccgcgtga                                                 18
```

```
<210> SEQ ID NO 7
<211> LENGTH: 21
<212> TYPE: DNA
<213> ORGANISM: homo sapiens

<400> SEQUENCE: 7
ucacucggcu ggauggagut t                                              21

<210> SEQ ID NO 8
<211> LENGTH: 21
<212> TYPE: RNA
<213> ORGANISM: homo sapiens

<400> SEQUENCE: 8
acuccaucca gccgagugaa g                                              21

<210> SEQ ID NO 9
<211> LENGTH: 21
<212> TYPE: RNA
<213> ORGANISM: homo sapiens

<400> SEQUENCE: 9
ucacucggcu ggauggagua a                                              21

<210> SEQ ID NO 10
<211> LENGTH: 21
<212> TYPE: RNA
<213> ORGANISM: homo sapiens

<400> SEQUENCE: 10
acuccaucca gccgagugaa a                                              21

<210> SEQ ID NO 11
<211> LENGTH: 21
<212> TYPE: RNA
<213> ORGANISM: homo sapiens

<400> SEQUENCE: 11
ucacugcgcu cgaugcagua a                                              21

<210> SEQ ID NO 12
<211> LENGTH: 21
<212> TYPE: RNA
<213> ORGANISM: homo sapiens

<400> SEQUENCE: 12
acugcaucga gcgcagugaa a                                              21

<210> SEQ ID NO 13
<211> LENGTH: 21
<212> TYPE: DNA
<213> ORGANISM: homo sapiens

<400> SEQUENCE: 13
ucacucggcu ggauggagut t                                              21

<210> SEQ ID NO 14
<211> LENGTH: 21
<212> TYPE: DNA
<213> ORGANISM: homo sapiens

<400> SEQUENCE: 14
acuccaucca gccgagugat t                                              21
```

```
<210> SEQ ID NO 15
<211> LENGTH: 21
<212> TYPE: DNA
<213> ORGANISM: homo sapiens

<400> SEQUENCE: 15
ggccuaccaa gugagggact t                                              21

<210> SEQ ID NO 16
<211> LENGTH: 21
<212> TYPE: DNA
<213> ORGANISM: homo sapiens

<400> SEQUENCE: 16
gucccucacu ugguaggcct t                                              21

<210> SEQ ID NO 17
<211> LENGTH: 22
<212> TYPE: RNA
<213> ORGANISM: homo sapiens

<400> SEQUENCE: 17
acggcagcgu gcagcucgcc ga                                             22

<210> SEQ ID NO 18
<211> LENGTH: 22
<212> TYPE: DNA
<213> ORGANISM: homo sapiens

<400> SEQUENCE: 18
ggcgagcugc acgcugccgu cc                                             22

<210> SEQ ID NO 19
<211> LENGTH: 21
<212> TYPE: RNA
<213> ORGANISM: homo sapiens

<400> SEQUENCE: 19
acugcaucga gcgcagugaa g                                              21

<210> SEQ ID NO 20
<211> LENGTH: 21
<212> TYPE: DNA
<213> ORGANISM: homo sapiens

<400> SEQUENCE: 20
ucacugcgcu cgaugcagut t                                              21

<210> SEQ ID NO 21
<211> LENGTH: 21
<212> TYPE: RNA
<213> ORGANISM: homo sapiens

<400> SEQUENCE: 21
uucagcaggc uugggcaag g                                               21

<210> SEQ ID NO 22
<211> LENGTH: 21
<212> TYPE: DNA
<213> ORGANISM: homo sapiens

<400> SEQUENCE: 22
uugcccacag ccugcugaat t                                              21
```

```
<210> SEQ ID NO 23
<211> LENGTH: 21
<212> TYPE: RNA
<213> ORGANISM: homo sapiens

<400> SEQUENCE: 23
uuccgaaggc ggugugcaag g                                              21

<210> SEQ ID NO 24
<211> LENGTH: 21
<212> TYPE: DNA
<213> ORGANISM: homo sapiens

<400> SEQUENCE: 24
uugcacaccg ccuucggaat t                                              21

<210> SEQ ID NO 25
<211> LENGTH: 18
<212> TYPE: DNA
<213> ORGANISM: homo sapiens

<400> SEQUENCE: 25
tcagcaggct gtgggcaa                                                  18

<210> SEQ ID NO 26
<211> LENGTH: 18
<212> TYPE: DNA
<213> ORGANISM: homo sapiens

<400> SEQUENCE: 26
acagctctcg gcatccga                                                  18

<210> SEQ ID NO 27
<211> LENGTH: 18
<212> TYPE: DNA
<213> ORGANISM: homo sapiens

<400> SEQUENCE: 27
tcagcaggct gtgggcaa                                                  18

<210> SEQ ID NO 28
<211> LENGTH: 18
<212> TYPE: DNA
<213> ORGANISM: homo sapiens

<400> SEQUENCE: 28
tccgaaggcg gtgtgcaa                                                  18

<210> SEQ ID NO 29
<211> LENGTH: 18
<212> TYPE: DNA
<213> ORGANISM: homo sapiens

<400> SEQUENCE: 29
ggccatccac agtcttct                                                  18

<210> SEQ ID NO 30
<211> LENGTH: 39
<212> TYPE: DNA
<213> ORGANISM: homo sapiens

<400> SEQUENCE: 30
cgcaagcttg gctgtgagca gtttctcagt atgaacttg                           39
```

```
<210> SEQ ID NO 31
<211> LENGTH: 34
<212> TYPE: DNA
<213> ORGANISM: homo sapiens

<400> SEQUENCE: 31
cttgagctcg ggaagaggcc ctagtgacca atag                    34
```

TREATMENT OF NEUROLOGICAL DISORDERS BY DSRNA ADMINISTRATION

PRIORITY INFORMATION

This application claims benefit of priority from Provisional Application No. 60/408,000, filed Sep. 4, 2002, Provisional Application No. 60/457,971, filed Mar. 27, 2003, International Application No. PCT/EP2003/009787, filed Sep. 3, 2003, Utility patent application Ser. No. 10/525,312, filed Mar. 24, 2005, now abandoned, and Divisional Utility patent application Ser. No. 11/779,098, filed Jul. 17, 2007 now U.S. Pat. No. 8,129,354, pending, all of which are incorporated herein by reference.

FIELD OF THE INVENTION

The present invention relates to methods of treatment neurological disorders and to a pharmaceutical composition for the treatment of chronic pain.

BACKGROUND OF THE INVENTION

Methods of inhibiting the expression of genes through short single-stranded oligonucleotides or oligoribonucleotides or modified oligonucleotides perfectly complementary to the target mRNA are known as "antisense". The use of antisense oligonucleotides (ASOs) as a tool to help elucidate gene function is well-described. Antisense oligonucleotides are also being evaluated as medicaments for a wide variety of diseases.

As an alternative to antisense, sequence-specific degradation of mRNAs with oligonucleotides can also be triggered by short RNA duplexes by an RNA interference (RNAi) mechanism. RNA interference is a process of sequence-specific, post-transcriptional gene silencing initiated by double-stranded RNA that is homologous in sequence to the silenced gene. The modulation of the function of a target nucleic acid by oligoribonucleotides which inhibit the expression of said target nucleic acid is generally referred to as "RNAi" or "RNA interference". Effective target-gene specific inhibition is usually achieved by short double-stranded (ds) oligoribonucleotide and with an overhang of approximately 2 nucleotides at the ends of at least 1 strand of the duplex. Such double-stranded oligoribonucleotides are known as short interfering RNAs (siRNAs) and have for instance been used as a tools to help elucidate gene function.

Great efforts are being made to develop oligonucleotides inhibiting the expression of specific target gene for therapeutic uses. One of the problems encountered is that, due to the special characteristics of oligonucleotides (such as for example high molecular weight, high amounts of negative charge, metabolic instability), delivery of free oligonucleotides to target tissues is generally much more limited in terms of the variety of disease target tissues, than for small molecule inhibitors: for instance, free oligonucleotides have low bioavailability when given orally to patients, systemic delivery of oligonucleotides leads to high levels of drug concentrated in a small number of organs, for example in liver, spleen and kidney, where the distribution is dependent on the format of the oligonucleotide (Feng et al., in 2000, European Journal of Pharmaceutical Sciences 10, 179-186). Delivery of oligonucleotides to the Central Nervous System (CNS) poses particular problems due to the blood brain barrier (BBB) that free oligonucleotides cannot cross. One means to deliver oligonucleotides into the CNS is intrathecal delivery. However, the oligonucleotides need also to be efficiently internalised into target cells of the CNS in order to achieve the desired therapeutic effect. Usually, delivery reagents such as liposomes, cationic lipids, nanoparticles forming complexes are utilized in order to aid the intracellular internalization of oligonucleotides into cells of neuronal origin. However, it is of considerable economic and technical advantage in the development of drugs if the desired pharmacological effects can be achieved without the use of tissue delivery reagents. So far, the only report describing short dsRNAs entering mammalian cells without the aid of a delivery reagent show a poor effect (Milhaud, Pierre G. et al., J. Interferon Res. (1991), 11(5), 261-5). We have now surprisingly found in accordance with the present invention, that intrathecally delivered siRNAs efficiently enter CNS tissues and are efficiently internalized into cells of the CNS system. Thus, the present invention now provides for the first time a method for functional downregulation of target genes by dsRNA in the CNS in vivo, thereby affecting the disease phenotype, by delivering siRNA to the CNS.

SUMMARY OF THE INVENTION

The present invention relates to a method to treat or ameliorate neurological disorders comprising intrathecal injection of an effective amount of a double stranded (ds) RNA into a subject in need, wherein said dsRNA inhibits the expression of a target gene. In a preferred embodiment the neurological disorder is selected from the group consisting of Alzheimer, Parkinson, multiple sclerosis, schizophrenia, epilepsy, depression and pain. In a more preferred embodiment, the disorder is chronic pain, preferably chronic neuropathic pain, cancer pain or osteoarthritis pain. In another preferred embodiment, the disorder is allodynia or hyperalgesia. Alternatively, the disorder is inflammatory chronic pain. In another preferred embodiment, the target gene is selected from the group consisting of purine receptors P1 or P2, Galanin R1 receptor, Vanilloid receptors 1, voltage gated calcium channel (N-type), the tetrodotoxin-resistant sodium channel Nav1.8 (PN3/SNS), TRPM8, IL-24, IL-20Ralpha or IL-20Rbeta. Particularly preferred are the P2 receptors, most preferred is $P_2X_3$ or $P_2X_2$. Further preferred target genes include Mob-5 or MMP7.

The subject in need is preferably mammalian. In one aspect of this invention the subject in need is rodent, preferably a rat. In a related aspect the subject in need is a monkey or a human.

In accordance with one aspect of the present invention, the amount of dsRNA that is intrathecally injected is 50 µg to 1500'4, preferably more than 180 µg, more preferably more than 200 µg, more than 300 µg or more than 400 µg.

In another aspect of the present invention, the dsRNA comprises a double-stranded region of 15 to 25 nt, preferably of 19 nt. In a related aspect, the dsRNA comprises a 3' overhang on the antisense or the sense strand or both strands of at least one nucleotide, preferably 1, 2, 3 or 4 nucleotides. In a preferred embodiment, the penultimate nucleotide of the overhang is complementary to the mRNA target strand. In another preferred embodiment, the overhang contains at least one modified nucleotide, a preferred modification is a 2-MOE modification. In a further preferred embodiment, the overhang comprises at least one UU and/or dTdT group. Also preferred is an overhang comprising UUUU or consisting of UUUU. In yet a further embodiment, the dsRNA comprises at least one modified linkage, preferred is at least one phosphorothioate linkage.

Another aspect of the present invention relates to the use of dsRNA for the treatment of chronic pain. The dsRNA is preferably administered by intrathecal injection to a subject in need and inhibits the expression of a target gene. In a preferred embodiment the chronic pain is chronic neuropathic pain, in another preferred embodiment the chronic pain is selected from the group consisting of cancer pain, osteoarthritis pain, allodynia or hyperalgesia. In further preferred embodiment the targeted gene is a gene encoding a purine receptors P1 or P2, Galanin R1 receptor, Vanilloid receptors 1, voltage gated calcium channel (N-type), the tetrodotoxin-resistant sodium channel Nav1.8 (PN3/SNS), TRPM8, IL-24, IL-20Ralpha or IL-20Rbeta, most preferred is a gene encoding $P_2X_3$ or $P_2X_2$. Further preferred genes include Mob-5 or MMP7.

Another aspect of the present invention relates to pharmaceutical compositions comprising an effective amount of dsRNA, wherein the dsRNA inhibits the expression of a target gene. These target genes are preferably overexpressed in chronic pain, preferably chronic neuropathic pain. Preferred target genes are the purine receptors P1 or P2, Galanin R1 receptor, Vanilloid receptors 1, voltage gated calcium channel (N-type), the tetrodotoxin-resistant sodium channel Nav1.8 (PN3/SNS), TRPM8, IL-24, IL-20Ralpha or IL-20Rbeta. Particularly preferred are the P2 receptors, most preferred is $P_2X_3$ or $P_2X_2$. Further preferred target genes include Mob-5 or MMP7. In another preferred embodiment, the pharmaceutical composition comprising an effective amount of a double stranded RNA is selected from the group consisting of SEQ ID Nos: 5, 6, 7, 8, 9, 10, 11, 12, 13, 14, 15 and 16.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication which might be used in connection with the invention.

In practicing the present invention, many conventional techniques in molecular biology are used. These techniques are well known and are explained in, for example, Harlow, E. and Lane, eds., 1988, "Antibodies: A Laboratory Manual", Cold Spring Harbor Press, Cold Spring Harbor, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein and in the appended claims, the singular forms "a", "an", and "the" include plural reference unless the context clearly dictates otherwise.

As used herein, "double-stranded ribonucleic acid (dsRNA)", as used herein, refers to an oligoribonucleotide or polyribonucleotide, modified or unmodified, and fragments or portions thereof, of genomic or synthetic origin or derived from the expression of a vector, which may be partly or fully double-stranded and which may be blunt-ended or contain a 5'- and/or 3'-overhang, and also may be of a hairpin form comprising a single oligoribonucleotide which folds back upon itself to give a double-stranded region.

As used herein "siRNA" denotes short interfering RNAs and refers to short double stranded ribonucleic acids useful for RNAi.

As used herein "inhibition" of gene expression means the reduction of the expression of said gene by at least 10%, 33%, 50%, 90%, 95% or 99%.

As used herein, the term "form" of or "format" of in relation to oligonucleotides refers to different chemical nature of the oligoribonucleotide, in particular to modifications as compared to naturally occurring ribonucleotides, such as for instance chemically modified 2'OH groups of the ribose moiety or the modified internucleosidic linkages such as phosphothioate linkages, or the modified nucleobases such as for example 5-methyl-C.

As used herein "Subject" refers to any human or nonhuman organism. Preferred are mammalian organisms.

As used herein the term nucleotide means ribonucleotide or deoxyribonucleotide, the terms oligonucleotide and oligoribonucleotide are interchangeable and refer, depending on the context, to modified or unmodified oligonucleotides comprising ribonucleotides and/or deoxyribonucleotides.

The present invention is based on the surprising discovery that intrathecally injected dsRNA inhibited the expression of a target gene thereby leading to a therapeutic effect in vivo, thus providing for the first time that a successful therapeutic treatment of a neurological disorder has been achieved by administration of dsRNA. Furthermore, the magnitude of the pharmacological effect from the siRNA on allodynia is much greater than that from the analogous antisense oligonucleotide. For instance, a dose limiting toxicity from use of the antisense oligonucleotide does not allow a pharmacological effect on allodynia to be observed, whereas no such dose limiting toxicity was observed from use of the siRNA, showing the possible advantages of using siRNAs over ASOs. The present invention makes therefore dsRNA available for the therapeutic treatment of neurological diseases.

In accordance with the present invention, the ribonucleic acid used for inhibition will have at least a partially double-stranded character, but may also be totally double-stranded. The RNA can be a single strand that is self-complementary or may comprise two or more separate complementary strands.

Particularly preferred in accordance with the present invention are short double-stranded RNAs, also termed siRNAs, having a length of 10 to 50 nucleotides, preferably 15 to 25 nucleotides. Yet more preferred are dsRNA's composed of oligoribonucleotides having a duplex length of 17 to 21 ribonucleotides. Even more preferred are oligoribonucleotides having a duplex length of 19 ribonucleotides.

The efficiency, i.e. the degree of inhibition of the target gene, is dependent on a number of different factors including the specificity of the dsRNA for its target sequence. In this context, specificity means homology, i.e. sequence identity between the dsRNA in the duplex region and the target sequence. It is understood by a person skilled in the art that 100% sequence identity is not required in order to achieve significant inhibition. Normally, at least 75% sequence identity between the dsRNA and the target sequence is sufficient in order to inhibit expression of the target nucleic acid. Preferred is a sequence identity of at least 80%, more preferred is a sequence identity of at least 90%. Most preferred is a sequence identity of at least 95% between the dsRNA and the target sequence. The best is clearly 100%. In order to target only the desired target mRNA, the siRNA reagent should have 100% homology to the target mRNA and at least 2 mismatched nucleotides to all other genes present in the cell or organism. Methods to analyze and identify ds RNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group). Another factor affecting the efficiency of the RNAi reagent is the target region of the target mRNA. The region of a target mRNA effective for inhibition by the RNAi reagent may be determined by experimentation. Most preferred mRNA target region would be the coding region. Also preferred are untranslated regions, particularly the 3'-UTR, splice junctions. For instance, transfection assays as described in Elbashir et al. (2001) may be performed for this purpose. A number of other suitable assays and methods exist in the art which are well known to a person skilled in the art.

The dsRNA according to the present invention may also contain modified nucleotide residues. As anyone having skill in the art of drug development would readily understand, siRNAs can exist in various formats as described in Tolen et al. 2002, Nucl. Acids Res. 30, 1757-1766; Elbashir S. M. et al, 2001 EMBO J., 20, 6877-6888; FEBS 2002, 521, 195-199; Current Biology 2001, 11, 1776-1780; Nature Biotech. 2002, 19, 497-500; Nature Biotech. 2002, 19, 505-508; Nucleic Acids Research 2002, 20, 1757-1766; Science 2002, 296, 5567, 550-553; Methods (San Diego, Calif., United States) 2002, 26(2), 199-213.

The dsRNA may be blunt ended or ligated at or on at least one end with either loops composed of ribonucleotides or deoxyribonucleotides or a chemical synthetic linker (WO00/44895). In a preferred embodiment, the ribonucleic acid contains 3'-end nucleotide overhangs on the antisense strand and/or the sense strands of the dsRNA of at least one ribonucleotide or deoxyribonucleotide, or modified nucleotide. Preferred are overhangs with 1, 2, 3 or 4 nucleotides. The overhangs may contain both ribonucleotide(s) and deoxyribonucleotide(s) which in addition may contain modified sugar moieties. The overhang may be of any sequence, but in a preferred embodiment, the overhang is complementary to the target mRNA strand. In another preferred embodiment the overhang contains at least one UU group or dTdT group. In another preferred embodiment, the overhang on the antisense strand has the penultimate overhanging nucleotide complementary to the mRNA target strand. Preferably, such an overhang is a 2-nucleotides overhang. In a further preferred embodiment, the overhang is composed of 4 Us.

In another preferred embodiment, the extreme 3'-position of the siRNA is a hydroxyl group. Additionally, the 5'-end may be a hydroxyl or phosphate group.

The sugar moieties may be unmodified or modified. Preferred modified sugar moieties oligonucleotides comprise one of the following at the 2' position: F; O—, S—, or N-alkyl; —O, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH2)$_n$O]$_m$CH3, O(CH2)$_n$OCH3, O(CH2)$_n$NH2, O(CH2)$_n$NR2, O(CH2)$_n$CH3, O(CH2)$_n$ONH2, and O(CH2)$_n$ON[(CH2)$_n$CH3)]2, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, SCH3, Cl, Br, CN, CF3, OCF3, SOCH3, SO3 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2 CH2 OCH3, also known as 2'-O—(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH2)2ON (CH3)$_2$ group, also known as 2'-DMAOE, 2'-methoxy (2'-O—CH3), 2'-aminopropoxy (2'-OCH2 CH2 NH2). A further preferred modification of this category is the bicyclic class of modifications known collectively as LNAs (Locked Nucleic Acids) as described in Rajwanshi et al., Angew. Chem. Int. Ed. 2000, 39, 1656-1659. One of skill in the art may use conventional methods to created such modified sugar structures. Representative United States patents that teach the preparation of such modified sugar structures include, but are not limited to, U.S. Pat. Nos. 4,981,957; 5,118,800; 5,700,920 and 5,969,116 each of which is incorporated by reference herein in its entirety.

The internucleoside linkage of the dsRNA may be the "normal" 3' to 5' phosphodiester linkage or contain at least one chemically modified linkage. In a preferred embodiment, the at least one overhanging nucleotides contains one or more modified linkages, whereas the double-stranded part of the oligonucleotide contains phosphodiester internucleoside linkages. Preferred modified linkages include but are not limited to, for example, those disclosed in U.S. Pat. Nos. 3,687,808; 4,469,863 and 5,625,050; each of which is incorporated by reference herein in its entirety. In a preferred embodiment the linkages are phosphorothioates, chiral phosphorothioates or phosphorodithioates. Techniques for the synthesis of compounds containing oligonucleotides with modified linkages as described above may be achieved using conventional methodologies, and are familiar to one of skill in the art.

The oligoribonucleotides may be prepared by chemical synthesis (Micura R., Angewandte Chemie, International Edition (2002), 41(13), 2265-2268) on commercially available or homemade oligonucleotide synthesizers using a number of different chemistries that are well known in the art. The oligonucleotide may also be prepared by in vitro transcription of a suitable template using for instance a commercially available kit such as the Silencer™ siRNA construction kit by Ambion. Alternatively, the oligoribonucleotides may be synthesized by transcription of siRNA's intracellularly from plasmids through both transient or stable transfection (Paddison P J et al., 2002, Genes and Development 16, 948-958, Paul et al., 2002, Nat. Biotech 29, 505-508).

The effect of dsRNA on gene expression will typically result in expression of the target gene being inhibited by at least 10%, 33%, 50%, 90%, 95% or 99% when compared to a cell not treated according to the present invention. Lower doses of administered material, lower concentrations of dsRNA in the cell and/or longer times after administration of dsRNA may result in inhibition at a lower level and/or in a smaller fraction of cells (e.g., at least 10%, 20%, 50%, 75%, 90%, or 95% of targeted cells). However, it is within the skill of the art to adapt conditions to provide the desired result. Quantitation of gene expression can be established by assessing the amount of the targeted gene product in the cell. For example, any mRNA transcribed from the target gene may be detected with a hybridization probe, or RT-PCR based methodologies, or translated polypeptide may be detected with an antibody raised against the encoded polypeptide.

The dsRNA is delivered in accordance with the present application by intrathecal injection (i.e. injection into the spinal fluid which bathes the brain and spinal chord tissue). Intrathecal injection of siRNA's into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal chord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

The amount of intrathecally injected dsRNA may vary from one target gene to another target gene and the appropriate amount that has to be applied may have to be determined individually for each target gene. Typically this amount will be in the range between 10 µg to 2 mg, preferably 50 µg to 1500 µg, more preferably 100 µg to 1000 µg. It has been found in accordance with the present invention that the dose limiting toxicity was at much lower amount of oligoribonucleotides for ASOs than for siRNA. For instance, whereas a dose limiting toxicity in the rat model was observed at 180 µg per day for ASOs, such a dose limiting toxicity was still absent at 400 µg per day for siRNAs. Thus, in a preferred embodiment of the present invention the dose of the intrathecally injected siRNA is at least 50 µg, more preferably at least 100 µg, more preferably at least 150 µg per day, more preferably at least 180 µg, more preferably at least 200 µg, more preferably at least 300 µg, most preferably at least 400 µg. It will be apparent to a person of skill in the art that the dose of intrathecally injected dsRNA will have to be adjusted appropriately in other organisms, the appropriate dose for humans, for instance, may be considerably higher.

In accordance with the present invention, the gene to be inhibited is expressed in the CNS. The target gene is often, but not always a gene which is misregulated, often upregulated in a given disease state. Examples for genes expressed in the CNS are genes for cytokines, genes causal for neuro-degeneration or regeneration such as Alzheimer or Parkinson or multiple sclerosis, viral genes from viruses infecting the CNS, genes causal for schizophrenia, epilepsy or depression. In a preferred embodiment the gene is causal for pain.

Pain is a term that encompasses a spectrum of clinical states. Acute pain serves as a physiological warning for a potentially tissue-damaging situation. Chronic pain occurs when the stimulus and pain are unrelated and the pain is no longer a protective mechanism. Chronic pain states are characterised by a number of clinical features. As well as spontaneous pain, patients may exhibit hyperalgesia (a greatly exaggerated response to a noxious mechanical, temperature or chemical), and allodynia (previously non-noxious stimuli are now perceived as painful). All these features result from a complex series of events involving changes in the function of sensory nerves in the periphery and in the processing of sensory information in the spinal cord and brain. These changes occur in response to direct neuronal damage or in response to mediators released during tissue damage or inflammation. Broadly speaking, chronic pain syndromes can be defined as inflammatory (also known as nociceptive) or neuropathic. Chronic inflammatory pain, as its name suggests, occurs during conditions in which there is underlying inflammation such as rheumatoid arthritis, burns, muscle damage or surgical wounds. Knowledge of the mechanisms underlying inflammatory pain has advanced considerably over recent years and it is known to involve a variety of mediators and their activation and sensitization of the peripheral terminals of sensory nerves and the consequent longer term changes in reactivity of spinal cord neurons. Chronic neuropathic pain is caused where there is a primary lesion or dysfunction of the nervous system and occurs, for example, during conditions such as trigeminal neuralgia, diabetic neuropathy, post-herpetic neuralgia, amputation or physical nerve damage. Chronic neuropathic pain results from damage to nerves by trauma, by diseases such as diabetes, herpes zoster, or late-stage cancer (see below), or by chemical injury (e.g. some anti-HIV drugs). It may also develop after amputation (including mastectomy), and is involved in some low-back pain. The mechanisms of chronic neuropathic pain are poorly understood but are thought to involve spontaneous firing of sensory nerves due to the novel expression of certain classes of ion channel, sprouting of sensory fibres into different layers of the spinal cord, and changes in the expression of various neurotransmitters and receptors in the sensory nerves and spinal cord. Traditionally chronic neuropathic pain has proven to be intractable and is resistant to the standard non-steroidal and opiate analgesics. There is therefore clearly an unmet clinical need for new analgesics to treat this type of pain. Cancer pain is the most common chronic pain syndrome (with probably inflammatory and neuropathic components). It is estimated that one third of patients with advanced cancer will develop skeletal metastases, particularly in breast, prostate and lung cancer. Metastatic bone disease commonly results in bone pain that is usually located to a discrete area and is described as a deep, boring sensation that aches and burns, accompanied by episodes of stabbing discomfort. The mechanisms responsible for bone cancer pain are unknown but it probably involves structural damage, periosteal irritation and nerve entrapment. There is evidence for the disruption of normal bone metabolism and the production of inflammatory prostaglandins and cytokines. Current treatment of bone cancer pain rests with opiates but the doses required results in unacceptable side-effects and at least 20% of patients still have uncontrolled pain. Novel, well tolerated and effective analgesics are desired to optimise the quality of life of these patients (Coleman R E (1997) *Cancer* 80; 1588-1594). Osteoarthritis pain is the most common form of chronic neuropathic pain (with probably inflammatory and neuropathic components) for which people visit general practitioners. Osteoarthritis is a chronic disease involving progressive structural changes in joint tissues, principally cartilage, synovium and subchondral bone. Typically, arthritic joints exhibit cartilage oedema and erosion, subchondral bone and synovial thickening, and formation of bony oesteophytes, all contributing to a deformation of the articular surface. The principal clinical symptom of osteoarthritis is pain, although the mechanisms underlying the chronic neuropathic pain in this condition are not understood.

Thus in another embodiment of the present invention, the gene is causal for chronic pain. Genes causal for pain can be determined using for instance the animal models described hereinbelow. Furthermore, a variety of genes are known to be implicated with chronic pain. For example genes encoding a member of the Vanilloid receptors 1 (NM_080706, NM_080705, NM_080705, NM_080704), or a voltage gated calcium channel (N-type), especially the alpha2 delta1 subunit a2d1 (NM_000722) and the a1B subunit (M94172 and M94173), or metabotropic glutamate receptor 1 (mGluR1) (Fundytus M. E. et al., British Journal of Pharmacology (2001), 132(1), 354-367) or the tetrodotoxin-resistant sodium channel Nav1.8 (PN3/SNS) (Yoshimura N. et al., Journal of Neuroscience (2001), 21(21), 8690-8696).

In a preferred embodiment of the present invention, the gene encodes a member of the family of the purine receptors $P_1$ or $P_2$ (Ralevic & Burnstock, Pharmacological Reviews 50 (1998), 413-492), preferably a member of the $P_2Y$ or $P_2X$ subclass. More preferred are the $P_2X_3$ or the $P_2X_2$ gene. Other examples of preferred genes include, but are not limited to Cathepsin S (NM_004079), TrpM8 (NM_024080), the Galanin R1 receptor (Jacoby A S et al., Genomics (1997) 45:3 496-508, NM_012958, NM_008082, NM_001480) or the genes described in U.S. Patent Application 60/369,893 such as for instance IL-24 (NM_006850), IL-20Ralpha or IL-20Rbeta (NM_014432 and AAZ20504).

In another preferred embodiment the gene encodes a member of the Mob-5 familiy. The term "Mob-5" as used herein refers to Mob-5, Genbank # AAF75553 as well as the human ortholog of this protein, Interleukin 24 (Genbank # AAA91780). The human ortholog of rat Mob-5 is also known as hMDA-7 as well as "suppression of tumorigenicity 16 (Jiang, H et al., Oncogene 11, 2477-2486, 1995). Included in the definition of the above genes are any and all forms of these polypeptides including, but not limited to, variants, partial forms, isoforms, precursor forms, full length polypeptides, fusion proteins or fragments of any of the above, from human or any other species. Apparent variants of Mob-5 include for instance c49a Genbank, Accession Number NM; AAB69171. Homologs of the above genes, which would be apparent to one of skill in the art, are also meant to be included in this definition. It is also contemplated that the term refers to the above genes isolated from naturally occurring sources of any species such as genomic DNA libraries as well as genetically engineered host cells comprising expression systems, or produced by chemical synthesis using, for instance, automated peptide synthesizers or a combination of such methods. Means for isolating and preparing such polypeptides are well understood in the art.

In another preferred embodiment the gene encodes MMP7 (matrilysin), a matrix metalloproteinase. The term "MMP7" refers to any and all forms of this polypeptide including, but not limited to, variants, partial forms, isoforms, precursor forms, the full length polypeptide, fusion proteins containing the MMP7 sequence or fragments of any of the above, from human or any other species. The sequence of rat MMP7 may be found in Genbank, Accession Number NM_012864. Homologs and orthologs of MMP7, which would be apparent to one of skill in the art, are meant to be included in this definition. It is also contemplated that the term refers to MMP7 isolated from naturally occurring sources of any species such as genomic DNA libraries as well as genetically engineered host cells comprising expression systems, or produced by chemical synthesis using, for instance, automated peptide synthesizers or a combination of such methods. Means for isolating and preparing such polypeptides are well understood in the art.

In a preferred embodiment the gene that is targeted is of mammalian origin, in a more preferred embodiment the gene is a rodent gene, most preferred is a rat gene. In another preferred embodiment the gene is a monkey or a human gene.

Another aspect of the present invention provides a pharmaceutical composition comprising an effective amount of a double stranded RNA inhibiting the expression of a gene causal for pain in an amount effective to treat chronic pain in a subject in need. In a preferred embodiment the gene is regulated in chronic neuropathic pain models). In a more preferred embodiment, the genes encode for a $P_1$ or $P_2$ Purine Receptor, more preferably for a receptor of the $P_2Y$ or $P_2X$ subclass. Most preferred are the $P_2X_3$ or the $P_2X_2$ gene. Other examples of preferred genes include, but are not limited to the Vanilloid receptors 1, voltage gated calcium channel (N-type), the tetrodotoxin-resistant sodium channel Nav1.8 (PN3/SNS), TRPM8, the Galanin R1 receptor or the genes described in U.S. Patent Application 60/369,893 such as for instance IL-24, IL-20Ralpha or IL-20Rbeta.

The pharmaceutical compositions disclosed herein useful for treating and/or ameliorating chronic pain, including chronic neuropathic pain, are to be administered to a patient at therapeutically effective doses to treat or ameliorate symptoms of such disorders. A therapeutically effective dose refers to that amount of the compound sufficient to result in amelioration of pain symptoms of chronic pain based on, for example, use of the McGill pain score (Melzack, R. Pain (1975) September. 1(3):277-299).

Compositions and formulations for intrathecal administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. The pharmaceutical formulations of the present invention may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with carriers.

The compositions of the present invention may be formulated into any of many appropriate dosage forms. The compositions of the present invention may for instance be formulated as suspensions in aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions suitable for use in the invention include compositions wherein the active ingredients are contained in an effective amount to achieve the intended purpose. The determination of an effective dose is well within the capability of those skilled in the art.

A therapeutically effective dose refers to that amount of active ingredient, i.e. double-stranded RNA in accordance with the present invention, useful to treat and/or ameliorate the pathological effects of chronic pain. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Guidance as to particular dosages and methods of delivery is provided in the literature and generally available to practitioners in the art.

Another aspect of the present invention provides the use of a double stranded RNA for the preparation of a medicament for the treatment of chronic pain. Preferably, the double stranded RNA inhibits purine receptors P1 or P2 or Galanin R1 receptor or IL-24 or IL-20Ralpha or IL-20Rbeta or MMP7, more preferably Mob-5 or P2X3 or P2X2. Said chronic pain is preferably cancer pain or osteoarthritis pain, more preferably hyperalgesia, most preferably allodynia.

The invention is further described by reference to the following examples. These examples are provided for illustration purposes and are not intended to be limiting.

EXAMPLES

The following experiments are used to illustrate the invention.

Materials and Methods.
Synthesis of Oligonucleotides Targeting P2X3 or Mob-5
Antisense Oligonucleotides (ASOs)

The ASOs against $P_2X_3$ and GAPDH are fully phosphorothioated 18-mers with nine nucleotides at the 3'-end modified with 2'-MOE groups and were synthesized using phosphoramidite chemistry (Eur. Pat. Appl. EP 992506 A2), HPLC-purified and characterized by electrospray mass spectrometry and capillary gel electrophoresis. For mismatch—containing control oligonucleotides, the approximate base composition of the match oligonucleotides was maintained (Table 1).

TABLE 1

Sequences of ASOs used in in vitro experiments

| | Target gene | Position in cds$^a$ | Relation to other ASOs$^b$ | Sequence$^c$ | GC content | SEQ ID |
|---|---|---|---|---|---|---|
| 5037 | rat $P_2X_3$ | 785-802 | | 5'-CsTsCsCsAsTsCsCsAsgscscsgsa sgstsgsa-3' | 61 | 1 |
| 5655 | rat $P_2X_3$ | | 4 MM to 5037 | 5'-CsTsAsCsAsGsCsCsAstscscsgscs gstsgsa-3' | 61 | 2 |
| 5660 | Rat GAPDH | 548-565 | | 5'-GsGsCsCsAsTsCsCsAscsasgstscs tstscst-3' | 55 | 3 |
| 5596 | unrelated | | | 5'-ccttaCsCsTsGsCsTsAsGsctggc-3' | 61 | 4 |

$^a$cds = coding sequence
$^b$MM = mismatch(es)

Unless otherwise stated, internucleotidic linkages are phosphodiester, N=deoxyribonucleoside, n=2'-O-(2-methoxyethyl) ribonucleoside, c=2'-O-(2-methoxyethyl) 5-methyl cytidine, t=2'-O-(2-methoxyethyl) 5-methyl uridine, s=phosphorothioate.

TABLE 2

Sequences of ASOs used in in vivo experiments

| | Target gene | Position in cds$^a$ | Relation to other ASOs$^b$ | Sequence$^c$ | GC | SEQ ID |
|---|---|---|---|---|---|---|
| 6798 | rat $P_2X_3$ | 785-802 | | 5'-ctccaTCCAGCCGagtga-3' | 61 | 5 |
| 6799 | rat $P_2X_3$ | | 4 MM to 5037 | 5'-ctacaGCCATCCGcgtga-3' | 61 | 6 |

All oligonucleotides are full phosphodiester 18 mers; N is deoxyribonucleoside, n=2'—O-(2-methoxyethyl) ribonucleoside, c=2'-O-(2-methoxyethyl) 5-methyl cytidine, t=2'-O-(2-methoxyethyl) 5-methyl uridine.

Oligoribonucleotides (siRNA's)

Modified synthetic oligoribonucleotides and modified antisense oligonucleotides described in this invention are prepared using standard phosphoramidite chemistry on ABI394 or Expedite/Moss Synthesizers (Applied Biosystems) for in vitro use and on OligoPilot II (Amersham Pharmacia Biotech) for in vivo purpose. Phosphoramidites are dissolved in acetonitrile at 0.05 M concentration (0.2M on Oligopilot II), coupling is made by activation of phosphoramidites by a 0.2 M solution of benzimidazolium triflate in acetonitrile. Coupling times are usually comprised between 3-6 minutes. A first capping is made using standard capping reagents. Sulfurization is made by using a 0.05 M solution of N-ethyl, N-phenyl-5-amino-1,2,4-dithiazol-3-thione for two minutes (described in EP-A-0992506). Oxidation is made by a 0.1M iodine solution in THF/Pyridine/Water (1:1:1) for two minutes. A second capping is performed after oxidation or sulfurization. Oligonucleotide growing chains are detritylated for the next coupling by 2% dichloroacetic acid in dichloromethane or dichloroethane. After completion of the sequences the support-bound compounds are cleaved and deprotected as "Trityl-on" by a Methylamine solution (41% aqueous methylamine/33% ethanolic methylamine 1:1 v/v) at 35° C. for 6 h for oligoribonucleotides and by a 32% aqueous Ammonia solution at 55° C. for 16 h for antisense oligonucleotides. Resulting suspensions are lyophilised to dryness. For oligoribonucleotides, 2'-O-silyl groups are removed upon treatment with 1M tetrabutylammonium fluoride 10 min at 50° C. and 6 h at 35° C. The obtained crude solutions are directly purified by RP-HPLC. The purified detritylated compounds are analysed by Electrospray Mass spectrometry and Capillary Gel Electrophoresis and quantified by UV according to their extinction coefficient at 260 nM. The oligoribonucleotides and antisense oligonucleotides directed against rat P2X3 and MOB-5 and their controls are shown in table 3 and 4, respectively.

TABLE 3

Oligoribonucleotides directed against rat P2X3.

| Name | Comment | Sequence (5'- to 3') | SEQ ID |
|---|---|---|---|
| NAS-8646 | Sense strand | UCACUCGGCUGGAUGGAGUtst | 7 |
| NAS-8647 | Antisense strand | ACUCCAUCCAGCCGAGUGAasg | 8 |
| NAS-7556 | Sense strand | UCACUCGGCUGGAUGGAGUasa | 9 |
| NAS-7557 | Antisense strand | ACUCCAUCCAGCCGAGUGAasa | 10 |
| NAS-7558 | 4 mismatch-sense strand | UCACUGCGCUCGAUGCAGUasa | 11 |
| NAS-7559 | 4 mismatch antisense strand | ACUGCAUCGAGCGCAGUGAasa | 12 |
| NAS-4882 | Sense strand | UCACUCGGCUGGAUGGAGUdTdT | 13 |
| NAS-4883 | Antisense strand | ACUCCAUCCAGCCGAGUGAdTdT | 14 |
| NAS-4884 | Sense strand | GGCCUACCAAGUGAGGGACdTdT | 15 |
| NAS-4885 | Antisense strand | GUCCCUCACUUGGUAGGCCdTdT | 16 |
| NAS-7126 | Sense strand | ACGGCAGCGUGCAGCUCGCCgsa | 17 |
| NAS-7127 | Antisense strand | GGCGAGCUGCACGCUGCCGUcsc | 18 |
| NAS-10104 | 4 mismatch of NAS-8646 (antisense) | ACUGCAUCGAGCGCAGUGAasg | 19 |
| NAS-10105 | 4 mismatch of NAS-8647 (sense) | UCACUGCGCUCGAUGCAGUtst | 20 |

RNAs NAS-8646 and NAS-8647, NAS-7556 and NAS-7557, NAS-4882 and NAS-4883, NAS-4884 and NAS-4885, NAS-7127 and 7126 as well as NAS-10104 and NAS-10105 are annealed together to give the siRNA's. NAS-8646 and NAS-8647 as well as NAS-10104 and 10105 have 2'-MOE ribonucleotides at the 3'-terminus of the oligoribonucleotide, and the sequence NAS 8647 is fully complementary to the target gene. NAS-7556 and NAS-7557 have 2'-MOE-A ribonucleotides at the 3'-terminus of the oligoribonucleotides; NAS-4882 and NAS-4883 have 2-dT deoxyribonucleotides at the 3'-terminus of the oligoribonucleotide; NAS-4884 and NAS-4885 have 2-dT deoxyribonucleotides at the 3'-terminus of the oligoribonucleotide. The oligoribonucleotides NAS-7126 and 7127 target an unrelated gene. Unless otherwise stated, internucleotidic linkages are phosphodiester, N=ribonucleoside, n=2'-O-(2-methoxyethyl) ribonucleoside, c=2'-O-(2-methoxyethyl) 5-methyl cytidine, t=2'-O-(2-methoxyethyl) 5-methyl uridine, dN=deoxyribonucleoside, s=phosphorothioate.

TABLE 4

Oligoribonucleotides and ASO's directed against rat MOB-5.

| Name | Comment | Sequence (5'- to 3') | SEQ ID |
|---|---|---|---|
| NAS-11535 | Antisense strand | UUC AGC AGG CUG UGG GCA AdGdG | 21 |
| NAS-11536 | Sense strand | UUG CCC ACA GCC UGC UGA AdTdT | 22 |
| NAS-11537 | 4 mismatch-antisense strand | UUC CGA AGG CGG UGU GCA AdGdG | 23 |
| NAS-11538 | 4 mismatch sense strand | UUG CAC ACC GCC UUC GGA AdTdT | 24 |
| NAS-8154 | ASO | tca gcdA dGdGdC dTdGdT dGgg caa | 25 |
| NAS-7428 | ASO | aca gcTs CsTsCs GsGsCs Astc cga | 26 |
| NAS-7429 | ASO | tca gcAs GsGsCs TsGsTs Gsgg caa | 27 |
| NAS-7443 | ASO | tcc gaAs GsGsCs GsGsTs Gstg caa | 28 |
| NAS-4660 | ASO | GsGsCs CsAsTs CsCsAs csasgs tscsts tscst | 29 |

RNAs NAS-11535 and NAS-11536, NAS-11537 and NAS-11538, are annealed together to give the siRNA's. The ASO NAS-4660 targets an unrelated gene. Unless otherwise stated, internucleotidic linkages are phosphodiester, N=ribonucleoside, dN=deoxyribonucleoside, n=2'-O(methoxyethyl) ribonucleoside, s=phosphorothioate.

Generation of a CHO Cell Line Expressing Rat-P2X3 (rP$_2$X$_3$—CHO)

Chinese hamster ovary cells (CHO-K1, ATCC CCL61) were stably transfected with a complete rat P2X3 cDNA sequence in the vector pRK7 (kindly obtained from John Wood; Chen, C. C et al. (1995). Nature 377, 428-430.). To be able to select for transfected cells, vector was co-electroporated in 10× excess with pMC1 neo (Stratagene) containing a Neomycin resistance gene. Cells were cultured in Minimal Essential Medium α (MEMα) supplemented with 10% (v/v) fetal bovine serum (FBS), 2-mM glutamine, and 10.000 IU/500 ml Penicillin/Streptomycin.

Generation of a Cho Cell Line Expressing Rat-P2X3/P2X2 (rP$_2$X$_{3/2}$—CHO)

rP2X3 insert was obtained by PCR using as template RT from total rat DRG RNA and using the oligos listed below:

```
P2X3-Hind-F:
                                   (SEQ ID No 30)
CGCAAGCTTGGCTGTGAGCAGTTTCTCAGTATGAACTTG P2X3-SacI-R:
                                   (SEQ ID No 31)
CTTGAGCTCGGGAAGAGGCCCTAGTGACCAATAG Note: the underlined sequence is a HindIII
restriction enzyme site added to the P2X3
complementary oligo. The SacI site in the
reverse primer was not used for cloning.
```

The PCR product was amplified using Advantage-HF2 Polymerase with thermal cycling at 94° C. for 30 s, 62° C. for 60 s, and 68° C. for 180 s for 6 cycles and 94° C. for 30 s, and 68° C. for 240 s for additional 29 cycles The PCR fragment was cloned in pGEM T-Easy (Promega) and sequenced with T7 and M13 reverse primers. The clone had the same sequence as the Genbank cDNA with accession number X91167.

rP2X3 insert was cut out of pGEM T-Easy by digestion with NotI and subcloned into pcDNA5/FRT linearized with NotI and dephosphorylated.

rP2X2 was obtained by digestion with BamHI and XhoI of a clone (see above). rP2X2 was subcloned into pcDNA5/FRT-Neo cut with the same enzymes.

2.5 μg of each DNA was used to transfect CHO Flp-In cells containing two integrated FRT sites using FuGENE 6 reagent. Cells transfected with rP2X2 have been selected with Geneticin 500 μg/ml, then transfected with rP2X3 and selected with Hygromycin-B 200 μg/ml to obtain the double transfectant.

Transfection of a Cell Line Expressing Rat-MOB-5 The cell line used was RBA (ATCC number 1747). It is rat skin derived, grows extremely tightly attached in a flattened out, skin-like morphology, and naturally expresses ras and mob-5 (known to be ras-downstream).

24 hours before transfection, 2×105 cells in a volume of 2 ml per well were plated into 6-well plates to yield 70-80% confluency. The day of transfection, a 2 fold stock transfector-solution was prepared by diluting Lipofectin®into serum-free OptiMEM (both GIBCO-BRL, Gaitherburg, Md.) (formula: 3 μl Lipofectin per 100 nM desired final oligonucleotide concentration into 1 ml OptiMEM) and incubating for 15 minutes at room temperature. This solution was then combined 1:1 with a 2 fold ASO-solution containing twice the desired final amount of ASO in OptiMEM. After incubating the transfection mixture for 15 minutes at room temperature to form the transfection complex, 2 ml were added to each of the previously aspirated well of cells. A Lipofectin reagent-only control and a normal cell control (untreated) were also included. After incubation for 4 hours at 37° C., 500 μl 50% FBS in MEMα was added to each well to obtain a final FBS concentration of 10%. The cultures were incubated at 37° C. in a humidified incubator with 5% CO2 for 24 hours before mRNA was harvested.

| Oligo, concentration | Average fg/50 ng total RNA |
| --- | --- |
| 7428, 400 nM | 5.03E+02 |
| 7428, 200 nM | 5.47E+02 |
| 7428, 100 nM | 7.13E+02 |
| 7428, 50 nM | 9.90E+02 |
| 7429, 400 nM | 1.73E+02 |
| 7429, 200 nM | 1.97E+02 |
| 7429, 100 nM | 4.63E+02 |
| 7429, 50 nM | 5.93E+02 |
| 7429, 12.5 nM | 1.09E+03 |
| 7443, 400 nM | 9.90E+02 |
| 7443, 200 nM | 1.21E+03 |
| 7443, 100 nM | 9.73E+02 |
| 7443, 50 nM | 6.77E+02 |
| 7443, 12.5 nM | 1.16E+03 |
| Lipofectin | 7.53E+02 |
| Untreated | 1.00E+03 |
| 4660, 400 nM | 8.40E+02 |
| 4660, 200 nM | 1.35E+03 |
| 4660, 100 nM | 1.04E+03 |

Electroporation of Mammalian Cells

CHO-rP2X2/3 cells were transfected with 0.15; 0.3; 0.6 or 1.2 nmole of ASO or siRNA duplex using standard electrotransfection (10$^6$ cells/125 ul in Biorad cuvette 0.4 cm, 250V, 0.3 μF, infinite resistance). Following electroporation, samples were immediately combined with 6 ml of the culture medium. In result, corresponding final concentration of ASO or siRNA reagents were 10, 50, 100 or 200 nM. Cells were plated on uncoated 96-well plates (Costar, Cat. #3904) and incubated at 37° C. for 24 h or 48 h, followed by RNA or protein extraction, respectively.

Total RNA Isolation and Assay by Quantitative Real Time PCR (Q-PCR)

Total RNA was extracted and purified using RNeasy 96 kit (Qiagen). Primer pairs and FAM-labelled TaqMan probes for real time PCR were designed using the Primer Express v 2.0 program (ABI PRISM, PE Biosystems). For the Q-PCR reaction, 50 ng total RNA was mixed with 5' and 3' primers (10 μM each), TaqMan probe (5 μM), MuLV reverse transcriptase (6.25 u, PE Biosystems), RNase Out RNase inhibitor (10 u, Life Technologies) and the components of the TaqMan PCR reagent kit (Eurogentec) in a total volume of 25 μl following the TaqMan PCR reagent kit protocol (Eurogentec). Reverse transcription and real time PCR was performed in a Gene-Amp Sequence Detector 5700 (PE Biosystems) as follows: 2 minutes reverse transcription at 50° C., 10 minutes denaturation at 95° C. followed by 50 cycles of denaturation for 15 sec at 95° C. and annealing and elongation for 1 min at 60° C. The relative quantitation of gene expression was calculated as described in the ABI PRISM 7700 user bulletin #2 (PE Biosystems).

Western Blotting

Cells grown in 6-well plates were washed with PBS and lysed with a buffer containing 11 mM NaCl, 5 mM KCl, 2.5 mM Tris pH7.4, 50 nM Va3VO4, 0.1% (v/v) Nonidet P-40 (100%), and 0.06 g protease inhibitor per 100 ml. Lysates were centrifuged for 10 min at 14000 rpm. Solubilized proteins in the supernatant were subjected to SDS-polyacrylamide gel electrophoresis through NuPAGE™ 4-12% Bis-Tris Gels in a NOVEX™ Mini-Cell system, followed by transfer to PVDF membranes (Millipore). The filters were blocked for 1 h with the blocking buffer contained in the ECF Western Blotting Kit (Amersham Pharmacia Biotech), washed several times in 1×PBS, pH 7.4 with 0.05% Tween 20, and incubated for 1 h with the primary anti-P2X3-antibody (purchased from Neuromics) in a dilution 1:5000. With several washes in between, the filters were then incubated with the secondary antibody, tertiary antibody and ECF substrate from the ECF Western Blotting Kit following the manufacturers suggestions. A quantification of the visualized bands was done with the software ImageQuant™ (Molecular Dynamics).

FLIPR Assay—Generation and Analysis of FLIPR Data

FLIPR experiments were performed as follows. Briefly, cells were loaded with fluo-4 AM in presence of 2.5 mM probenicid for 30-45 min, washed twice with HBSS (Gibco)+ 20 mM HEPES, and transferred to the fluorescence reader (FLIPR, Molecular Devices). Drug plates were prepared at 5× the final concentration. Fluo-4 fluorescence was measured at a rate of 0.5 Hz for 3 min. Agonists were applied after 20 points baseline detection.

FLIPR sequence files were analyzed using Igor Pro (Wavemetrics). Baseline was set as the average of 20 points before drug addition, peak was detected as maximal signal in the 50 data points after drug addition. Relative change of fluorescence (dF/F) was determined as (peak−baseline)/(baseline) values. These values were averaged, and for concentration-response analysis further analyzed by fitting a sigmoidal hill equation to the data. Data are presented as mean+/−S.E.M. or EC50 values as mean (95% confidence interval).

Animal Models of Chronic Pain

In vivo animal models of chronic neuropathic pain include the following:

Seltzer Model

In the Seltzer model (Seltzer et al. (1990) Pain 43: 205-218) rats are anaesthetised and a small incision made midway up one thigh (usually the left) to expose the sciatic nerve. The nerve is carefully cleared of surrounding connective tissues at a site near the trochanter just distal to the point at which the posterior biceps semitendinosus nerve branches off the common sciatic nerve. A 7-0 silk suture is inserted into the nerve with a ⅜ curved, reversed-cutting mini-needle, and tightly ligated so that the dorsal ⅓ to ½ of the nerve thickness is held within the ligature. The muscle and skin are closed with sutures and clips and the wound dusted with antibiotic powder. In sham animals the sciatic nerve is exposed but not ligated and the wound closed as in nonsham animals.

Chronic Constriction Injury (CCI) Model

In the CCI model (Bennett, G. J. and Xie, Y. K. Pain (1988) 33: 87-107) rats are anaesthetised and a small incision is made mid-way up one thigh (usually the left) to expose the sciatic nerve. The nerve is cleared of surrounding connective tissue and four ligatures of 4/0 chromic gut are tied loosely around the nerve with approximately 1 mm between each, so that the ligatures just barely constrict the surface of the nerve. The wound is closed with sutures and clips as described above. In sham animals the sciatic nerve is exposed but not ligated and the wound closed as in nonsham animals.

Chung Model

In contrast to the Seltzer and CCI models which involves damage to peripheral nerves, the Chung model involves ligation of the spinal nerve. (Kim, S. O. and Chung, J. M. Pain (1992): 50:355-363). In this model, rats are anesthetized and placed into a prone position and an incision is made to the left of the spine at the L4-52 level. A deep dissection through the paraspinal muscles and separation of the muscles from the spinal processes at the L4-52 level will reveal part of the sciatic nerve as it branches to form the L4, L5 and L6 spinal nerves. The L6 transverse process is carefully removed with a small rongeur enabling visualisation of these spinal nerves. The L5 spinal nerve is isolated and tightly ligated with 7-0 silk suture. The wound is closed with a single muscle suture (6-0 silk) and one or two skin closure clips and dusted with antibiotic powder. In sham animals the L5 nerve is exposed as before but not ligated and the wound closed as before.

Axotomy Model

The Axotomy model involves complete cut and ligation of the sciatic nerve. The nerve endings form neuromas but there is no behavioral correlate in this model as the nerve is not allowed to regenerate, and the foot is permanently denervated. (Kingery and Vallin, Pain 38, 321-32, 1989)

High Sciatic Lesion Model

In this model, the sciatic nerve is punctured in the region of the iliac arch. Although there is no overt damage to the nerve, local swelling produces an increase in pressure on the nerve as it passes under the iliac arch. This model resembles conditions often seen in the clinic.

Chronic Inflammatory Pain Model

The Complete Freund's Adjuvant-induced mechanical hyperalgesia may be used as a model of chronic inflammatory pain (Stein, C. et al. Pharmacol. Biochem. Behav. (1988) 31:445-451). In this model, typically a male Sprague-Dawley or Wistar rat (200-250 g) receives an intraplantar injection of 25 μl complete Freund's adjuvant into one hind paw. A marked inflammation occurs in this hind paw. Drugs are generally administered for evaluation of efficacy, 24 hours after the inflammatory insult, when mechanical hyperalgesia is considered fully established.

Behavioral Index

In all chronic pain models (inflammatory and neuropathic) mechanical hyperalgesia is assessed by measuring paw withdrawal thresholds of both hindpaws to an increasing pressure stimulus using an Analgesymeter (Ugo-Basile, Milan). Mechanical allodynia is assessed by measuring withdrawal thresholds to non-noxious mechanical stimuli applied with von Frey hairs to the plantar surface of both hindpaws. Thermal hyperalgesia is assessed by measuring withdrawal latencies to a noxious thermal stimulus applied to the underside of each hindpaw. With all models, mechanical hyperalgesia and allodynia and thermal hyperalgesia develop within 1-3 days following surgery and persist for at least 50 days. For the assays described herein, drugs may be applied before and after surgery to assess their effect on the development of hyperalgesia, particularly approximately 14 days following surgery, to determine their ability to reverse established hyperalgesia.

The percentage reversal of hyperalgesia is calculated as follows:

$$\% \text{ reversal} = \frac{\text{postdose threshold} - \text{predose threshold}}{\text{naive threshold} - \text{predose threshold}} \times 100$$

In the experiments disclosed herein, Wistar rats (male) are employed in the chronic neuropathic pain models described above. Rats weigh approximately 120-140 grams at the time of surgery. All surgery is performed under enflurane/$O_2$ inhalation anaesthesia.

In all cases the wound is closed after the procedure and the animal allowed to recover.

In all but the axotomy model, a marked mechanical and thermal hyperalgesia and allodynia develops in which there is a lowering of pain threshold and an enhanced reflex withdrawal response of the hind-paw to touch, pressure or thermal stimuli. After surgery the animals also exhibit characteristic changes to the affected paw. In the majority of animals the toes of the affected hind paw are held together and the foot turned slightly to one side; in some rats the toes are also curled under. The gait of the ligated rats varies, but limping is uncommon. Some rats are seen to raise the affected hind paw from the cage floor and to demonstrate an unusual rigid extension of the hind limb when held. The rats tend to be very sensitive to touch and may vocalise. Otherwise the general health and condition of the rats is good.

Treatment of Animal Models of Chronic Pain

Oligonucleotide reagents used in the animal models have been named as the following:

ASO: NAS-6798 (SEQ. ID 5), MSO: NAS-6799 (SEQ. ID 6), P2X3 RNAi: NAS-8646 and

NAS-8647 (SEQ. ID 7 and 8 respectively), P2X3 RNAi missense: NAS-10104 and NAS-10105 (SEQ. ID 19 and 20 respectively).

Intrathecal Delivery of siRNA.

dsRNA was administered intrathecally via an indwelling cannula in a buffer (100 mM KA 2 mM MgAc, 0.1749 g HEPES free acid (M=238.3), 0.2102 g NaCl per 100 ml RNase free water; pH 7.63 at 20° C. with KOH). Rats were anaesthetised and an incision made in the dorsal skin just lateral to the midline and approximately 10 mm caudal to the ventral iliac spines. A sterile catheter (polyethylene PE10 tubing) was inserted via a guide cannula (20 gauge needle) and advanced 3 cm cranially in the intrathecal space approximately to the L1 level. The catheter was then connected to an osmotic mini-pump (Alzet) delivering P2X3 receptor or MOB-5 receptor siRNA, missense siRNA or saline (1 μl/h, 7 days) which was inserted subcutaneously in the left or right flank. The incision was closed with wound clips and dusted with antibiotic powder. Experiments determined 180 as well as 220 μg/day to have no signs of toxicity. Mechanical hyperalgesia was assessed on day 0, day 6 before administration of α,β-methylene-ATP (Me-ATP) and 1 h post Me-ATP by measuring paw withdrawal thresholds of both hindpaws to an increasing pressure stimulus using an Analgesymeter (Ugo-Basile, Milan). The cut-off was set at 250 g and the end-point taken as paw withdrawal, vocalisation or overt struggling. Each animal was tested only once, in random order. The statistical significance of mechanical hyperalgesia data obtained from the different experimental animal groups was analysed using ANOVA followed by Tukey's HSD test. 1.0 μmol (in 10 μl) of Me-ATP was given intraplantar (ipl) to the contralateral hindpaw on the final day of the experiment. 1.0 h post administration, paw withdrawal thresholds to mechanical hyperalgesia were measured.

Example 1

Transfection of siRNA's into Cell Lines Expressing Rat $P_2X_3$

| treatment | RNA [%] remaining | SD |
| --- | --- | --- |
| OF | 99 | 4 |
| MM NAS-7558/7559 | 100 | 2 |
| NAS-7556/7557 | 18 | 2 |
| NAS-8646/8647 | 11 | 3 |
| NAS-4882/4883 | 11 | 6 |
| NAS-4884/4885 | 21 | 4 |

Efficacy of P2X3 mRNA inhibition by variety of siRNA's delivered by Oligofectamine-mediated transfection of CHO-rP2X3 cells. Q-PCR analysis. OF: control with Oligofectamine alone; mmNAS-7558/7559: control with mismatch; NAS-7556/7557: siRNA with optimised (as NAS-5037) sequence and noncomplementary moe/ps overhangs; NAS-8646/8647: as NAS-7556/7557 but with mRNA-complementary overhangs; NAS-4882/4883: siRNA with optimised (as NAS-5037) sequence and noncomplementary dTdT overhangs; NAS-4884/4885: siRNA with a sequence designed according to criteria described in Harborth, J. et al. (2001). J. Cell Science 114: 4557-4565.

Example 2

| Treatment | % P2X3 protein remaining |
| --- | --- |
| No treatment | 90 |
| Oligofectamine alone | 100 |
| siRNA NAS-7556/7557 | 25 |
| P2X3 mismatch NAS-7558/7559 | 100 |
| SiRNA unrelated | 100 |

$P_2X_3$ protein inhibition by the siRNA NAS-7556/7557, plotted as %. After SDS-PAGE, protein was blotted, immunodetected with anti-$P_2X_3$ antibody (Neuromics), blot bands were quantified with the software ImageQuant™, and expression levels were plotted as % against control siRNA.

Example 3

| | % mRNA | | SD | |
| --- | --- | --- | --- | --- |
| Treatment | ASO | siRNA | ASO | siRNA |
| untreated | 100 | 100 | 2.4 | 2.4 |
| MM | 71 | 77 | 3.0 | 5.6 |
| 10 nM | 78 | 54 | 5.0 | 2.9 |
| 50 nM | 71 | 34 | 2.4 | 4.1 |
| 100 nM | 63 | 28 | 3.9 | 4.6 |
| 200 nM | 44 | 22 | 5.2 | 8.5 |

Comparison of mRNA inhibition of $P_2X_3$ expression at 4 doses by the siRNA NAS-8646/8647 and its antisense analogue NAS-5037. Electroporation of the CHO cell line expressing recombinant P2X3 and recombinant P2X2. mRNA was measured with real-time quantitative PCR.

Example 4

| treatment | % mRNA | | SD | |
|---|---|---|---|---|
| | ASO | siRNA | ASO | siRNA |
| untreated | 100 | 100 | 4 | 4 |
| MM | 122 | 109 | 3 | 3 |
| 10 nM | 108 | 83 | 3 | 5 |
| 50 nM | 88 | 67 | 4 | 2 |
| 100 nM | 82 | 43 | 3 | 2 |
| 200 nM | 67 | 31 | 2 | 3 |

FLIPR functional assay. Downregulation of functional response to 10 μM Me-ATP agonist by transfection of ASO-NAS-5037 and siRNA NAS-8646/8647 into a CHO-r P2×2/P2X3 cell line at concentrations of 10, 50, 100, and 200 nM 48 h prior to agonist treatment as compared to untreated control and to mismatch controls (MSO-5655 and siRNA NAS-7557/7558).

Example 5

Effect of P2X3 siRNA's on hyperalgesia in rats with agonist-induced pain

| Left paw | Paw threshold (g) | | | |
|---|---|---|---|---|
| (agonist injected) | vehicle | P2X3 ASO 180 μg | P2X3 RNAi 180 μg | P2X3 RNAi 220 μg |
| Naïve day 0 | 101.7 ± 2.0 | 103.3 ± 2.0 | 98.3 ± 4.1 | 101.7 ± 2.0 |
| Predose day 6 | 100.0 ± 0.0 | 101.7 ± 2.0 | 101.7 ± 5.4 | 98.3 ± 2.0 |
| 1 h | 58.3 ± 2.0 | 83.3 ± 2.0 | 75.0 ± 3.5 | 81.7 ± 7.4 |

The effect of P2X3 RNAi administered as an intrathecal infusion over 6 days on naïve rats on mechanical allodynia. On day 6: ipl injection of 1 μmol Me-ATP and measurement of Von Frey thresholds of these treated rats. Vehicle: isotonic buffer, n=6/treatment group.

Example 6

Effect of P2X3 siRNA's on allodynia in rats with agonist-induced pain

| Left paw | Von Frey threshold (g) | | | |
|---|---|---|---|---|
| (agonist injected) | vehicle | P2X3 ASO 180 μg | P2X3 RNAi 400 μg | P2X3 RNAi missense 400 μg |
| Naïve day 0 | 15 ± 0 | 12.6 ± 1.5 | 14.2 ± 0.8 | 13 ± 1.3 |
| Predose day 6 | 15 ± 0 | 14 ± 1.0 | 14.2 ± 0.8 | 14.1 ± 0.8 |
| 15 min post-dose | 4.2 ± 0.9 | 4.4 ± 1.0 | 8.8 ± 1.3 | 3.3 ± 1.0 |
| 30 min post-dose | 4.5 ± 0.8 | 6 ± 0.9 | 9.1 ± 1.3 | 4.7 ± 1.0 |
| 60 min post-dose | 6.3 ± 0.8 | 6.4 ± 1.2 | 9.1 ± 1.3 | 5 ± 0.9 |

The effect of P2X3 RNAi administered as an intrathecal infusion over 6 days on naïve rats on mechanical allodynia. On day 6: ipl injection of 1 μmol Me-ATP and measurement of Von Frey thresholds of these treated rats. Vehicle: isotonic buffer, n=6/treatment group.

Example 7

Effects of P2X3 siRNA on mechanical hyperalgesia in rats with neuropathic pain (Seltzer model)

| | Paw withdrawal thresholds (g) | | | | |
|---|---|---|---|---|---|
| | | Neuropathic | | | |
| Day | Naïve vehicle | vehicle | P2X3 RNAi missense 400 μg | P2X3 RNAi 400 μg | P2X3 ASO 180 μg |
| 0 | 102.5 ± 1.33 | 102.5 ± 1.33 | 104.375 ± 1.13 | 101.25 ± 0.81 | 102.5 ± 0.94 |
| 11 | 103.75 ± 1.57 | 58.12 ± 1.62 | 60 ± 1.64 | 60 ± 2.11 | 57.5 ± 1.63 |
| 12 | 101.87 ± 1.61 | 61.25 ± 1.57 | 61.25 ± 1.83 | 80 ± 0.94 | 75 ± 0.94 |
| 13 | 102.5 ± 1.33 | 62.5 ± 2.11 | 60 ± 1.33 | 81.87 ± 2.09 | 74.37 ± 2.40 |
| 14 | 103.12 ± 0.91 | 61.87 ± 1.88 | 64.37 ± 2.74 | 81.87 ± 1.87 | 76.25 ± 1.25 |
| 15 | 103.75 ± 0.81 | 63.75 ± 1.25 | 64.37 ± 4.27 | 81.87 ± 1.61 | 75.62 ± 1.13 |
| 16 | 101.875 ± 1.62 | 64.37 ± 1.13 | 65 ± 4.00 | 83.12 ± 0.91 | 73.12 ± 2.10 |
| 17 | 102.5 ± 1.64 | 61.87 ± 2.09 | 63.12 ± 4.21 | 79.37 ± 1.75 | 71.25 ± 2.63 |
| 17.5 | 101.25 ± 1.56 | 63.75 ± 1.25 | 62.5 ± 3.13 | 81.25 ± 1.25 | 71.87 ± 2.30 |

Four groups of rats were ligated on the left hind limb on day 0 and base line mechanical hyperalgesia was measured daily. An additional unligated group (naïve) was set up as control. Rats were cannulated on day 11 and infused with vehicle, RNAi, RNAi missense or ASO for a further 6 days. Paw withdrawal thresholds (left paw) were measured daily. Vehicle: isotonic buffer, n=8/treatment group.

Example 8

Effects of P2X3 siRNA on mechanical allodynia in rats with neuropathic pain (Seltzer model)

| | Von Frey thresholds (g) | | | |
|---|---|---|---|---|
| | | Neuropathic | | |
| Day | Naive vehicle | vehicle | P2X3 RNAi missense 400 µg | P2X3 RNAi 400 µg | P2X3 ASO 180 µg |
| 0 | 13.75 ± 0.81 | 13.75 ± 0.81 | 13.75 ± 0.81 | 13.75 ± 0.81 | 15 ± 0 |
| 11 | 14.37 ± 0.63 | 3.87 ± 1.17 | 3.25 ± 0.84 | 4.37 ± 1.28 | 4.125 ± 1.00 |
| 12 | 13.75 ± 0.81 | 4.37 ± 1.28 | 3.25 ± 1.04 | 6.5 ± 1.05 | 4.5 ± 0.98 |
| 13 | 13.12 ± 0.91 | 4.75 ± 1.19 | 3.25 ± 0.99 | 8 ± 1.13 | 4.25 ± 1.03 |
| 14 | 14.37 ± 0.62 | 5.25 ± 0.92 | 3.25 ± 0.99 | 7.25 ± 1.19 | 4.25 ± 0.96 |
| 15 | 14.37 ± 0.62 | 4.75 ± 1.25 | 3.25 ± 0.75 | 7.75 ± 1.10 | 4.25 ± 0.96 |
| 16 | 15 ± 0 | 4.5 ± 0.98 | 4 ± 0.75 | 7 ± 1.06 | 3.5 ± 0.73 |
| 17 | 14.37 ± 0.62 | 5 ± 1 | 4 ± 0.75 | 7 ± 1 | 4.25 ± 0.95 |

Four groups of rats were ligated on the left hind limb on day 0 and base line mechanical allodynia was measured daily. An additional unligated group (naïve) was set up as control.

Rats were cannulated on day 11 and infused with vehicle, RNAi, RNAi missense or ASO for a further 6 days. Von Frey thresholds on the left paw were measured daily. Vehicle: isotonic buffer, n=8/treatment group.

Example 9

Effects of MOB-5 siRNA on mechanical hyperalgesia in rats with neuropathic pain (Seltzer model)

| | Paw withdrawal thresholds (g) | | | |
|---|---|---|---|---|
| | | Neuropathic | | |
| Day | Naive vehicle | vehicle | MOB-5 RNAi missense 400 µg | MOB-5 RNAi 400 µg |
| 0 | 101.4 ± 2.4 | 103.1 ± 1.3 | 99.4 ± 1.1 | 100 ± 1.9 |
| 10 | 101.4 ± 1.8 | 60.6 ± 1.5 | 62.5 ± 1.3 | 60 ± 1.6 |
| 11 | 102.1 ± 1.5 | 61.9 ± 1.3 | 66.2 ± 1.6 | 67.5 ± 2.1 |
| 12 | 102.1 ± 2.1 | 62.5 ± 0.9 | 65.5 ± 1.1 | 75 ± 2.1 |
| 13 | 105 ± 2.2 | 63.7 ± 1.5 | 66.9 ± 1.6 | 81.2 ± 2.9 |
| 14 | 102.1 ± 2.1 | 64.4 ± 1.5 | 62.5 ± 2.3 | 78.7 ± 4.2 |
| 15 | 102.1 ± 1.8 | 62.5 ± 0.94 | 61.9 ± 2.3 | 74.4 ± 2.7 |
| 16 | 102.1 ± 1.5 | 62.5 ± 0.94 | 58.7 ± 2.3 | 75 ± 2.3 |

Four groups of rats were ligated on the left hind limb on day 0 and base line mechanical hyperalgesia was measured. An additional unligated group (naïve) was set up as control. Rats were cannulated on day 10 and infused with vehicle, RNAi or missense for a further 6 days. Paw withdrawal thresholds (left paw) were measured daily. Vehicle: isotonic buffer, n=8/treatment group. The right paw for each group were also measured but showed no difference in paw withdrawal threshold to naïve animals.

Example 10

Effects of MOB-5 siRNA on mechanical allodynia in rats with neuropathic pain (Seltzer model)

| | Von Frey thresholds (g) | | | |
|---|---|---|---|---|
| | | Neuropathic | | |
| Day | Naive vehicle | vehicle | MOB-5 RNAi missense 400 µg | MOB-5 RNAi 400 µg |
| 0 | 14.3 ± 0.7 | 12 ± 1.2 | 11.9 ± 0.9 | 12.9 ± 1.0 |
| 10 | 15 ± 0 | 5.9 ± 1.5 | 3 ± 0.6 | 6.1 ± 1.5 |
| 11 | 14.3 ± 0.7 | 5.5 ± 1.1 | 2.7 ± 0.5 | 5.7 ± 0.9 |
| 12 | 14.3 ± 0.7 | 4.2 ± 1.2 | 2.5 ± 0.5 | 6.2 ± 0.8 |
| 13 | 14.3 ± 0.7 | 4.2 ± 1.2 | 2.7 ± 0.5 | 5.7 ± 0.8 |
| 14 | 15 ± 0 | 4.0 ± 1.0 | 2.5 ± 0.3 | 6.7 ± 0.8 |

-continued

| | Von Frey thresholds (g) | | | |
| | | | Neuropathic | |
| Day | Naive vehicle | vehicle | MOB-5 RNAi missense 400 μg | MOB-5 RNAi 400 μg |
| --- | --- | --- | --- | --- |
| 15 | 12.1 ± 1.0 | 3.7 ± 0.7 | 2.5 ± 0.3 | 6.5 ± 0.7 |
| 16 | 12.1 ± 1.0 | 4.2 ± 0.7 | 3.2 ± 0.6 | 6.7 ± 0.7 |

Four groups of rats were ligated on the left hind limb on day 0 and base line mechanical allodynia was measured. An additional unligated group (naïve) was set up as control. Rats were cannulated on day 10 and infused with vehicle, RNAi or missense for a further 6 days. Von Frey thresholds on the left paw were measured daily. Vehicle: isotonic buffer, n=8/treatment group. The right paw for each group were also measured but showed no difference in paw withdrawal threshold to naïve animals.

The invention claimed is:

1. A method to treat or ameliorate pain in a subject in need thereof, the method comprising the step of intrathecal injection of an effective amount of a siRNA into the subject, wherein said siRNA inhibits the expression of the Mob-5 gene or an ortholog thereof by an RNA interference mechanism, and wherein more than 180 μg of siRNA per 120-140 grams of body weight per day are intrathecally injected.

2. A method according to claim 1, wherein the subject is human and the ortholog is human.

3. A method according to claim 1, wherein the subject is rat.

4. A method according to claim 1, wherein said pain is chronic pain.

5. A method according to claim 4, wherein said chronic pain is selected from the group consisting of cancer pain, osteoarthritis pain, allodynia and hyperalgesia.

6. A method according to claim 1, wherein at least 200 μg of siRNA per 120-140 grams of body weight per day are intrathecally injected.

7. A method according to claim 1, wherein the siRNA comprises a double-stranded region of 15 to 25 nt.

8. A method according to claim 1, wherein the siRNA comprises a 3' overhang on the antisense or the sense strand, or both strands, of at least one nucleotide.

9. A method according to claim 8, wherein the overhang contains at least one modified nucleotide.

10. A method according to claim 8, wherein the overhang comprises at least one 2'-MOE modified nucleotide.

11. A method according to claim 8, wherein the overhang comprises 4 Uracils.

12. A method according to claim 1, wherein the siRNA comprises at least one phosphorothioate linkage.

13. A method of reducing the expression of the Mob-5 gene or an ortholog thereof in a subject in need thereof, the method comprising the step of intrathecal injection of an effective amount of a siRNA into the subject inhibits the expression of the Mob-5 gene or an ortholog thereof by an RNA interference mechanism, and wherein more than 180 μg of siRNA per 120-140 grams of body weight per day are intrathecally injected.

14. The method of claim 13, wherein the subject is human and the ortholog is human.

15. The method of claim 13, wherein the subject is rat.

16. The method according to claim 13, wherein said pain is chronic pain.

17. The method according to claim 16, wherein said chronic pain is selected from the group consisting of cancer pain, osteoarthritis pain, allodynia and hyperalgesia.

18. The method according to claim 13, wherein the siRNA comprises a 3' overhang on the antisense or the sense strand, or both strands, of at least one nucleotide.

19. The method according to claim 18, wherein the overhang contains at least one modified nucleotide.

20. The method according to claim 18, wherein the overhang comprises at least one 2'-MOE modified nucleotide.

21. The method according to claim 18, wherein the overhang comprises 4 Uracils.

22. The method according to claim 13, wherein the siRNA comprises at least one phosphorothioate linkage.

* * * * *